United States Patent
Soe

(10) Patent No.: US 9,321,801 B2
(45) Date of Patent: Apr. 26, 2016

(54) METHOD FOR REDUCING THE AMOUNT OF STERYL GLYCOSIDE IN AN OIL OR FAT

(75) Inventor: Jorn Borch Soe, Tilst (DK)

(73) Assignee: DUPONT NUTRITION BIOSCIENCES APS, Copenhagen (DK)

( * ) Notice: Subject to any disclaimer, the term of this patent is extended or adjusted under 35 U.S.C. 154(b) by 632 days.

(21) Appl. No.: 13/003,154

(22) PCT Filed: Jul. 8, 2009

(86) PCT No.: PCT/IB2009/006379
§ 371 (c)(1),
(2), (4) Date: Apr. 6, 2011

(87) PCT Pub. No.: WO2010/004423
PCT Pub. Date: Jan. 14, 2010

(65) Prior Publication Data
US 2011/0173876 A1 Jul. 21, 2011

(30) Foreign Application Priority Data
Jul. 9, 2008 (GB) .................................. 0812559.3

(51) Int. Cl.
| | |
|---|---|
| C10L 1/00 | (2006.01) |
| C12N 9/24 | (2006.01) |
| C07J 17/00 | (2006.01) |
| C12P 7/64 | (2006.01) |
| C11B 3/00 | (2006.01) |
| C12N 9/34 | (2006.01) |
| C11B 3/04 | (2006.01) |
| C11B 3/06 | (2006.01) |
| C11C 3/00 | (2006.01) |

(52) U.S. Cl.
CPC ............... *C07J 17/005* (2013.01); *C11B 3/001* (2013.01); *C11B 3/003* (2013.01); *C11B 3/006* (2013.01); *C11B 3/04* (2013.01); *C11B 3/06* (2013.01); *C11C 3/003* (2013.01); *C12N 9/2405* (2013.01); *C12N 9/2428* (2013.01); *C12P 7/649* (2013.01); *C12P 7/6445* (2013.01); *C12P 7/6454* (2013.01); *C12Y 302/01003* (2013.01); *Y02E 50/13* (2013.01); *Y02P 20/52* (2015.11); *Y02P 30/20* (2015.11)

(58) Field of Classification Search
USPC ............... 44/301, 307; 435/200, 262
See application file for complete search history.

(56) References Cited

U.S. PATENT DOCUMENTS

| | | | |
|---|---|---|---|
| 2002/0116868 A1* | 8/2002 | Westfall et al. | .................. 44/301 |
| 2005/0130281 A1 | 6/2005 | Both et al. | |

FOREIGN PATENT DOCUMENTS

| | | | |
|---|---|---|---|
| EP | 1531182 | * | 5/2005 |
| EP | 2098585 | | 9/2009 |
| WO | WO 2005/066351 A | | 7/2005 |
| WO | WO 2006/008508 A | | 1/2006 |
| WO | WO2006008508 | | 1/2006 |
| WO | WO 2007/076163 A | | 7/2007 |
| WO | WO2007076163 | * | 7/2007 |

OTHER PUBLICATIONS

EP1531182 Claims; May 2005.*
EP1531182 Description; May 2005.*
Nyström, et al., "Enzymatic hydrolysis of steryl ferulates and steryl glycosides," European Food Research and Technology: Zeitschrift für lebensmitteluntersuchung and forschung A, 2007, vol. 227, No. 3, p. 727-733. XP019621735.
Clausen, "Enzymatic oil-degumming by a novel microbial phospholipase," European Journal of Lipid Science and Technology, 2001, vol. 103, No. 6, p. 333-340. XP001039221.
Oil Mill Gazetteer, vol. 111 Jul. 2005 pp. 2-4 "Enzymatic Degumming improves Oil Refining in China".
Phillips KM et al., Analysis of steryl glucosides in foods and dietary supplements by solid-phase extraction and gas chromatography, (2005), Journal of Food Lipids, 12(2), 124-140.
European Patent Office Examination Report EP application 09 786 077.9 mailed Dec. 19, 2014.
Bing Feng et al., "Purification, characterization, and substrate specificity of a glucoamylase with steroidal saponin-rhamnosidase activity from Curvularia lunata," Applied Microbiology and Biotechnology, Sep. 6, 2007, pp. 1329-1338.

* cited by examiner

*Primary Examiner* — Ellen Mcavoy
*Assistant Examiner* — Chantel Graham
(74) *Attorney, Agent, or Firm* — Steptoe & Johnson LLP

(57) ABSTRACT

The present invention relates to a method for reducing the amount of steryl glycoside in an oil or fat (e.g. a biofuel substrate) and/or a biofuel, the method comprising admixing one or more enzymes with an oil or fat comprising steryl glycoside; such that said one or more enzymes degrades the steryl glycoside. The one or more enzymes is preferably an enzyme which is capable of hydrolysing the glycosidic bond in a steryl glycoside. Suitably the enzyme may be a glycosidase enzyme and/or a β-glucosidase and/or an amyloglucosidase.

29 Claims, 1 Drawing Sheet

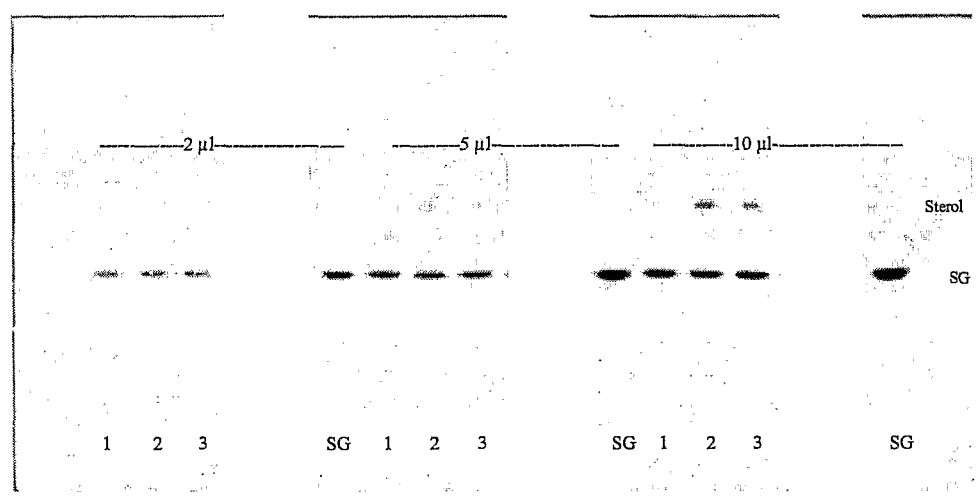

METHOD FOR REDUCING THE AMOUNT OF STERYL GLYCOSIDE IN AN OIL OR FAT

CLAIM OF PRIORITY

This application claims priority under 35 U.S.C. 371 to International Application No. PCT/IB2009/006379, filed on Jul. 8, 2009, which claims priority to Great Britain Application No. 0812559.3, filed on Jul. 9, 2008, each of which is hereby incorporated by reference in its entirety.

FIELD OF THE PRESENT INVENTION

The present invention relates to a method for reducing the steryl glycoside content of an oil or fat (including a biofuel substrate for example a biodiesel substrate and/or a biofuel (including a biodiesel) by degrading the steryl glycoside using an enzyme.

The present invention also relates to an oil or fat (including a biofuel substrate, for example a biodiesel substrate) or a biofuel (including a biodiesel) produced by the methods of the present invention.

BACKGROUND OF THE PRESENT INVENTION

Recent concerns about security of energy resources and global warming have let to increased focus on the use of biofuels as a renewable resource. Biodiesel has been produced for 15 to 20 years and, until recently, has mainly been produced in Europe and mostly from rapeseed oil.

In recent years biodiesel production in the USA has increased significantly. With the expansion of biodiesel production in the USA, an increasing amount of soy oil (and/or other oils which contain varying amounts (sometime minor amounts) of steryl glycoside) is/are being used as a raw material for the biodiesel production.

It has recently come to light that biodiesel and biodiesel blends made from oil containing steryl glycoside can cause problems. For example, the presence of steryl glycoside in a biofuel may cause precipitation therein which is undesirable as it may result in filter clogging and/or causing an engine fuelled by the biofuel to stop. Precipitation may be the precipitation of the steryl glycoside or may be the precipitation of the steryl glycoside in combination with other components within the biofuel. It has been suggested that precipitation of the steryl glycosides may exacerbate precipitation and/or aggregation of other components in the biofuel.

The steryl glycoside may precipitate during storage over the course of several weeks. Therefore, although freshly produced biodiesel may meet the quality standards, after some week's storage the biodiesel may no longer pass the filter test.

It has been found that steryl glycoside is not easy to remove during production of biofuel (including biodiesel).

Producers of biodiesel have tried to overcome these problems by additional filtration steps and by centrifugation.

WO2007/076163 relates to the use of specific filtration procedures to remove steryl glycoside. In particular WO2007/076163 discloses a process for removing steryl glycosides from biodiesel by adding adsorbents, filter aids, boric acid, soap, sucrose, sugar, glucose, sodium chloride, citric acid, magnesium silicate, clay, diatomaceous earth, lecithin, granular clay, granular glucose, granular sugar, protein, textured vegetable protein, carbon, cellulose, solutions comprising boric acid, silica hydrogel and combinations thereof that are allegedly capable of removing steryl glycosides from the biodiesel. One disadvantage of this procedure is that it introduces an extra filtration step which can be costly and/or time consuming.

Another disadvantage of removing steryl glycosides by filtration or centrifugation is that it may be necessary to wait for the steryl glycosides to precipitate and/or aggregate before they can be removed from the oil.

The present invention aims to overcome a problem related to the presence of steryl glycoside in biofuels.

SUMMARY ASPECTS OF THE PRESENT INVENTION

Aspects of the present invention are presented in the claims and in the following commentary.

It has surprisingly been found that steryl glycoside can be removed from an oil or fat (such as a biofuel substrate, e.g. a biodiesel substrate) by the use of an enzyme capable of hydrolysing the glycosidic bond in a steryl glycoside and/or an acylated steryl glycoside, in particular the enzyme may be a glycosidase enzyme as defined here, for instance a β-glucosidase enzyme and/or an amyloglucosidase enzyme.

BRIEF DESCRIPTION OF THE DRAWINGS

FIG. 1 is an HPTLC of steryl glycoside (SG) incubated with 1) Water. 2 Grindamyl Ca 150, 3) AMG 8000 (Danisco A/S).

DETAILED ASPECTS OF THE PRESENT INVENTION

According to a first aspect of the present invention there is provided a method for reducing the amount of (or removing) steryl glycoside in an oil or fat (e.g. a biofuel substrate) and/or a biofuel, the method comprising admixing one or more enzymes with an oil and/or fat comprising steryl glycoside; such that said one or more enzymes degrades the steryl glycoside.

In a second aspect of the present invention there is provided a use of one or more enzymes in an oil or fat (e.g. in a biofuel substrate) for reducing the amount of (or removing) steryl glycoside.

According to a third aspect of the present invention there is provided one or more of an oil or fat (e.g. a biofuel substrate) or a biofuel obtainable (preferably obtained) by a method according to the present invention.

In a fourth aspect of the present invention there is provided one or more of an oil or fat (e.g. a biofuel substrate) or a biofuel, which oil or fat (e.g. biofuel substrate) and/or biofuel has a reduced amount of steryl glycoside compared with a comparable oil or fat which has not undergone enzyme treatment in accordance with the present invention.

According to another aspect of the present invention there is provided an enzyme composition comprising one or more enzymes capable of hydrolysing the glycosidic bond in a steryl glycoside and/or an acylated steryl glycoside, suitably one or more glucosidase enzymes, suitably one or more β-glucosidase, suitably one or more amyloglucosidase enzymes, for use in the production of biofuel.

Suitably the one or more enzymes for use in the methods and/or uses of the present invention may be one or more of the following enzymes: an enzyme that is capable of carrying out the cleavage of a glycosidic bond, especially an enzyme capable of carrying out the cleavage of the glycosidic bond of a steryl glycoside and/or an acylated steryl glycosidase, an enzyme capable of carrying out the following reaction:

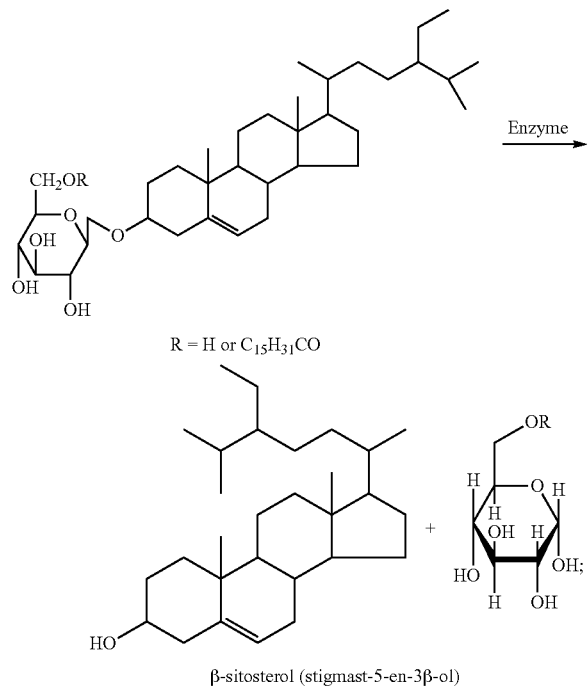

β-sitosterol glucosides

R = H or C₁₅H₃₁CO

β-sitosterol (stigmast-5-en-3β-ol)

a glycosidase (E.C. 3.2.1.X), for example a β-glucosidase, an amyloglucosidase (E.C. 3.2.1.3).

Suitably the one or more enzymes for use in the present invention may be one or more of the following enzymes: an enzyme capable of hydrolysing the glycosidic bond in a steryl glycoside and/or an acylated steryl glycoside.

Suitably the one or more enzymes for use in the present invention may be one or more of the following enzymes: a glucosidase, for example a β-glucosidase or an amyloglucosidase or another enzyme having amyloglucosidase activity.

In one embodiment suitably an enzyme used in the present invention may be the pectinase Grindamyl™ Ca 150 (available from Danisco A/S). Without wishing to be bound by theory—it is believed that Grindamyl™ Ca 150 is an enzyme formulation where as well as pectinase activity there are a number of side activities. One of these side activities may be a β-glucosidase activity. Without wishing to be bound by theory it is believed that it is this β-glucosidase side activity which renders the enzyme composition Grindamyl™ Ca 150 capable of hydrolysing the glycosidic bond in a steryl glycoside and/or an acylated steryl glycoside.

Suitably an enzyme used in the present invention may be the amyloglucosidase AMG8000 (available from Danisco A/S).

In one embodiment an amyloglucosidase enzyme or an enzyme capable of carrying out the cleavage of the glycosidic bond of a steryl glycoside and/or acylated steryl glycoside is admixed with an oil or fat (e.g. a biofuel substrate), water and an enzyme capable of carrying out interesterification of oil and an alcohol.

In one embodiment suitably the oil or fat (e.g. a biofuel substrate) may be a biodiesel substrate (i.e. an oil or fat suitably for biodiesel formation).

In one embodiment, suitably the oil or fat may be a biofuel substrate (e.g. the biodiesel substrate)

In another embodiment, suitably the oil or fat may be an oil or fat for use in the food industry.

In a further embodiment, the oil or fat with the steryl glycoside removed therefrom and/or reduced steryl glycoside content may be used as a biofuel substrate and/or it may be used in the food industry.

In one embodiment, oil or fat (e.g. the biofuel substrate, for example the biodiesel substrate) may be a vegetable oil or vegetable fat.

In a further embodiment the oil or fat (e.g. the biofuel substrate, for example the biodiesel substrate) may be an oil or fat (suitably a vegetable oil or a vegetable fat) comprising steryl glycoside.

In another embodiment the oil or fat (e.g. the biofuel substrate, for example the biodiesel substrate) may be a vegetable oil selected from the group consisting of rapeseed oil, canola oil, soya (soybean) oil, rice bran oil, palm oil, corn oil, cottonseed oil, sunflower oil, safflower oil, nasturtium seed oil, mustard seed oil, olive oil, sesame oil, peanut oil, babassu nut oil, castor oil, palm kernel oil, low erucic acid rapeseed oil, lupin oil, jatropha oil, coconut oil, flaxseed oil, evening primrose oil, jojoba oil, shea nut oil or camelina oil.

In one embodiment preferably oil or fat (e.g. the biofuel substrate, for example the biodiesel substrate) may be a vegetable oil selected from the group consisting of rapeseed oil, canola oil, soya (soybean) oil, rice bran oil, palm oil, corn oil, cottonseed oil and sunflower oil.

In one embodiment suitably the biofuel may be biodiesel.

In one embodiment suitably the method may further comprise a degumming step, for instance a water-degumming step.

As used herein, a "water-degumming step" may be typically carried out by mixing 0.5-3% w/w of hot water with warm (60-90° C.) crude oil. Usual treatment periods are 30-60 minutes. The water-degumming step removes the phosphatides and mucilaginous gums which become insoluble in the oil when hydrated. The hydrated phosphatides and gums can be separated from the oil by settling, filtration or centrifugation—centrifugation being the more prevalent practice. The essential object in said water-degumming process is to separate the hydrated phosphatides from the oil. The mixing of hot water into the oil, described above, should herein be understood broadly as mixing of an aqueous solution into the oil according to standard water-degumming procedures in the art.

In another embodiment the method according to the present invention may further comprise an enzymatic degumming step.

In another embodiment the method according to the present invention may comprise an enzymatic degumming step wherein water is added to the oil or fat (e.g. biofuel substrate). Suitably the amount of water that is added during the enzymatic degumming step may be between about 0.1% to about 5% by weight of the oil (typically about 2% w/w enzyme/oil).

Suitably the amount of steryl glycoside is reduced using one or more enzymes in accordance with the present invention before, during and/or after the degumming step, e.g. the water degumming step and/or enzymatic degumming step. In other words, the admixing of the one or more enzymes (e.g. glucosidase—such as an amyloglucosidase) with the oil or fat (e.g. the biofuel substrate) occurs before, during and/or after the degumming step (e.g. the water degumming step and/or the enzymatic degumming step).

In a further embodiment the method according to the present invention may comprise a interesterification step.

In one embodiment, suitably the method may further comprise a centrifugation step.

Suitably the amount of steryl glycoside is reduced using one or more enzymes in accordance with the present invention before, during and/or after the centrifugation step. In other words, the admixing of the one or more enzymes (e.g. a glucosidase, such an amyloglucosidase) with the oil or fat (e.g. the biofuel substrate) occurs before, during and/or after centrifugation.

In one embodiment the method may be performed at between about 30° C. and 70° C., suitably between about 40-60 ° C., suitably between about 45-55 ° C., suitably at about 50° C.

Suitably the method may be carried out on raw (crude) oil.

Suitably the method may be carried out on an oil or fat (e.g. a biofuel substrate, such as a biodiesel substrate) during processing to biofuel (or biodiesel).

In one embodiment suitably one or more enzymes may be admixed with an oil (preferably a vegetable oil, e.g. a biofuel substrate) during the refining of the oil.

When the oil or fat (e.g. the biofuel substrate) undergoes a degumming process, the enzyme may be added during the degumming process wherein water is added to the oil or fat (e.g. the biofuel substrate). In one embodiment the enzyme may be added during an enzymatic degumming process.

When the oil or fat (e.g. biofuel substrate) undergoes an interesterification process (this may be carried out using enzymes which catalyse the interesterification reaction between the oil and methanol)—the enzyme of the present invention may also be added to the oil or fat during the enzymatic interesterification process.

In another embodiment suitably one or more enzymes and water may be admixed with a oil or fat (preferably a vegetable oil, e.g. a biofuel substrate).

In another embodiment suitably one or more enzymes may be admixed with a oil or fat (preferably a vegetable oil, e.g. a biofuel substrate) simultaneously with the oil undergoing an enzymatic degumming process, suitably an enzymatic degumming process wherein water is added to the oil or fat (e.g. biofuel substrate).

In another embodiment suitably one or more enzymes may be admixed with an oil or fat (preferably a vegetable oil, e.g. a biofuel substrate) simultaneously with the oil or fat undergoing an interesterification (preferably an enzymatic interesterification) step.

In one embodiment preferably the oil or fat (e.g. biofuel substrate) obtainable (preferably obtained) by the method according to the present invention has less steryl glycoside therein compared with an untreated oil or fat (e.g. biofuel substrate) (i.e. the same oil or fat (e.g. biofuel substrate) but which has not been treated in accordance with the present invention).

In one embodiment preferably the biofuel (e.g. biodiesel) obtainable (preferably obtained) by the method according to the present invention has less steryl glycoside therein compared with an untreated biofuel (e.g. biodiesel) (i.e. the same biofuel but which has not been treated in accordance with the present invention.

Without wishing to be bound by theory, the enzyme used in the present invention may remove steryl glycoside by hydrolysing it to form a free sterol and a sugar or an acylated sugar (depending upon whether the steryl glycoside is unacylated or acylated).

In some embodiments the present invention may comprise a step of removing any free sterol formed in the oil or fat. By way of example the free sterol may be removed during, before or after further processing the oil or fat. This may be particularly advantageous when the oil or fat is to be used in the food industry.

Suitably the method and uses of the present invention remove at least 20%, 50%, 80% of the steryl glycoside in the oil or fat (e.g. biofuel substrate).

Measuring the Amount of Steryl Glycoside in the Oil or Fat (e.g. Biofuel Substrate) or the Biofuel The amount of steryl glycoside in the oil or fat (e.g. biofuel substrate) and/or the biofuel may be determined by any conventional process.

The amount of steryl glycoside in an oil or fat may be determined, for example, by solid-phase extraction and gas chromatography as described in Phillips et al. (2005), Journal of Food Lipids, 12(2), 124-140.

The quality of the biodiesel may be measured using a standard filter blocking test such as that according to ASTM method D 2068 "Standard Test Method for Filter Blocking Tendency of Distillate Fuel Oils". When the steryl glycerides are removed in accordance with the present invention the biodiesel is a better quality when measured using said standard filter blocking test compared with a comparable control biodiesel which is the same except that is has not undergone the method of the present invention.

When referring to "reducing" or a "reduction" of the amount of steryl glycoside in an oil or fat (e.g. a biofuel substrate) or a biofuel—the term "reducing" or "reduction" means in comparison to a comparable oil or fat (e.g. biofuel substrate) or biofuel which is the same as the claimed biofuel substrate or biofuel except that no enzyme(s) in accordance with the present invention have been added.

Advantages

The present invention provides a simple and cost effect method for the removal of steryl glycoside from oil and fat (particularly oils or fats which are to be used as a biofuel substrate or in the food industry) and/or from the biofuel (e.g. from the biodiesel).

One advantage of the present invention is that the steryl glycoside can be removed from the oil or fat (e.g. biofuel substrate) or from the biofuel (e.g. from the biodiesel) before the steryl glycoside precipitates.

Another advantage of the present invention is that the steryl glycoside can be removed from the oil or fat (e.g. a biofuel substrate) during processing.

Another advantage of the present invention is that a centrifugation or filtration step is not essentially required to remove the steryl glycoside from the oil or fat (e.g. biofuel substrate) or from the biofuel (e.g. from the biodiesel).

A further advantage of the present invention is that it is an effective method of removing steryl glycosides from an oil or fat (e.g. a biofuel substrate and/or a food oil or fat) and/or from a biofuel.

A further advantage of the present invention is that specialised or expensive centrifugation or filtration equipment is not required to remove steryl glycosides from the oil or fat (e.g. the biofuel substrate) or the biofuel (e.g. biodiesel).

Another advantage of the present invention is that a biofuel (in particular a biodiesel) is produced that can pass a "filter blocking test" even after storage for example for several weeks.

Steryl Glycoside

Steryl glycosides consist of one carbohydrate unit linked to the hydroxyl group of one sterol molecule. The sterol moiety could be campesterol, stigmasterol, sitosterol, brassicasterol and dihydrositosterol. The sugar moiety can be composed of glucose, xylose and even arabinose (Graminae). When the sugar moiety is glucose the steryl glycoside may be referred to as a steryl glucoside. In the present invention the term steryl glycoside is meant to encompass steryl glucoside.

In one embodiment the steryl glycoside is a steryl glucoside.

The sugar moiety may be linked to the sterol moiety via a glycosidic bond. The sugar moiety can be acylated at the carbon 6 position.

Steryl glycosides occur naturally in oils and fats (particularly vegetable oils and fats) in acylated and non-acylated forms. In the acylated form they are very soluble in the oil. In the present invention the term "steryl glycosides" means both acylated and unacylated steryl glycosides. Similarly the term "steryl glucosides" as used herein means both acylated and unacylated steryl glucosides.

During the process for conversion of an oil or fat (e.g. a biofuel substrate) to a biofuel (e.g. biodiesel), acylated steryl glycosides are converted to non-acylated steryl glycosides which have a high melting point and are less soluble in biodiesel or diesel fuel mixes.

Steryl glycosides (e.g. steryl glucosides) can precipitate to form dispersed fine solid particles in the fuel which can not simply be heated to allow them to pass through a blocked diesel filter. These particles may also promote the crystallisation of other fuel components, which can exacerbate problems of cold-crystallising components such as monoglycerides.

Steryl glycosides can form aggregates at any temperature, not just at cold temperatures. Even low levels, such as 10-90 ppm of steryl glycoside in biodiesel can form aggregates.

Steryl glycosides have a high melting point around 240° C. and therefore aggregates containing them can not be easily removed by melting.

The amount of steryl glycoside in crude vegetable oils can vary.

The amount of steryl glycosides in crude soybean oil is higher than in some other oils that are commonly used to make biodiesel, for example, rape seed, corn, cotton or sunflower oil.

By way of example only the level of steryl glycoside present in different vegetable oils is presented in the table below:

| Vegetable oil | Level of steryl glycoside (ppm) |
| --- | --- |
| Soy oil | 2300 |
| Corn oil | 500 |
| Sunflower oil | 300 |

Biofuel

Biofuel (which may also be referred to as agrofuel or agrifuel) is broadly defined herein as solid, liquid or gas fuel comprising, or derived from, recently dead biological material, most commonly plants. This distinguishes it from fossil fuel, which is derived from long dead biological material.

Biofuel can be theoretically produced from any (biological) carbon source. The most common by far is photosynthetic plants that capture solar energy. Many different plants and plant-derived materials are used for biofuel manufacture.

Biofuels are used globally and biofuel industries are expanding in Europe, Asia and the Americas. The most common use for biofuels is as liquid fuels for automotive transport. The use of renewable biofuels provides increased independence from petroleum and enhances energy security.

In one embodiment preferably the biofuel taught herein is a liquid fuels. The biofuel is preferably a liquid biofuel for transportation.

In one embodiment preferably the biofuel is a biodiesel.

Oil or Fat

Suitably the oil or fat may be a vegetable oil or fat or a processed vegetable oil or fat.

Suitably the oil or fat (preferably a vegetable oil or fat) for use in the present invention may be any oil or fat (preferably a vegetable oil or fat) comprising a steryl glycoside.

In one embodiment the oil or fat is an oil or fat which comprises at least 10ppm steryl glycoside.

The vegetable oil or fat for use in the present invention may be selected from one or more of the group consisting of: rapeseed oil, canola oil, soya (soybean) oil, rice bran oil, palm oil, corn oil, cottonseed oil, sunflower oil, safflower oil, nasturtium seed oil, mustard seed oil, olive oil, sesame oil, peanut oil, babassu nut oil, castor oil, palm kernel oil, low erucic acid rapeseed oil, lupin oil, jatropha oil, coconut oil, flaxseed oil, evening primrose oil, jojoba oil, shea nut oil or camelina oil.

The vegetable oil or fat for use in the present invention may be selected from one or more of the group consisting of: rapeseed oil, soy oils (which may also be called soyabean oil or soya oil), sunflower oil, canola oil, palm oil, rice bran oil, cotton oil and corn oil.

In one embodiment preferably the vegetable oil is soy oil.

In one embodiment preferably the oil may be an oil derived from algae.

In one embodiment the oil or fat (preferably the vegetable oil or fat) is suitable for the production of a biofuel, e.g. such as biodiesel and is thus considered a "biofuel substrate" or a "biodiesel substrate" respectively.

In some embodiments the oil or fat may be an animal fat and/or oil.

The oil or fat may be a crude oil or may be a processed oil. The term "processed oil" as used herein means an oil which has undergone some form of processing such as refining, bleaching, degumming, interesterification and/or deodorising.

In some embodiments the oil or fat may be an hydrogenated oil, an oil or fat derivative, or a fraction of an oil or fat.

In one embodiment preferably the oil or fat is a crude oil (preferably a crude vegetable oil) and/or a processed oil (preferably a processed vegetable oil).

In one embodiment preferably the oil or fat is to be used in the production of a biofuel and is therefore considered to be a biofuel substrate, suitably a biodiesel substrate.

In another embodiment the oil or fat may be used in the production of an edible oil or fat for the food industry, in which case the oil or fat is considered to be an edible oil or fat.

Biofuel Substrate

A biofuel substrate as used herein means any substance which may be converted into a biofuel, preferably a liquid biofuel. Suitably the biofuel substrate is recently dead biological material, most commonly plants.

In one embodiment preferably the biofuel substrate is an oil or fat.

Biodiesel

Biodiesel is similar to conventional petroleum diesel but it is produced from vegetable or animal fats and oils. It is currently increasing in popularity because it is seen as a renewable and carbon neutral fuel that could be less damaging to the environment than fossil fuels. It can be used as an alternative fuel to petroleum diesel in diesel engines and is commonly used as an additive to petroleum diesel. Pure biodiesel is classified as B100 but it is often blended with petroleum diesel so that a diesel that is 20% biodiesel would be B20.

The majority of biodiesel is produced by interesterification of triglycerides (e.g. oil and/or fats) with an alcohol, often in the presence of a catalyst, to form esters and glycerol. The catalyst is usually sodium or potassium hydroxide. As methanol and ethanol are the most commonly used alcohols in commercial biodiesel production most commercially produced biodiesel comprises methyl or ethyl esters of fatty acids.

Biodiesel is a biofuel and has the chemical name fatty acid methyl (or ethyl) ester (FAME).

In one embodiment the biodiesel may be a biodiesel produced from vegetable and/or animal fats or oils blended with petroleum diesel.

In one embodiment preferably the biofuel referred to herein is a biodiesel.

Food

In one embodiment the oil or fat may be used as—or in the preparation of—a food. Here, the term "food" is used in a broad sense—and covers food for humans as well as food for animals (i.e. a feed). In a preferred aspect, the food is for human consumption.

The food may be in the form of a solution or as a solid—depending on the use and/or the mode of application and/or the mode of administration.

In one aspect the oil or fat prepared in accordance with the present invention may be used in a foodstuff selected from one or more of the following: eggs, egg-based products, including but not limited to mayonnaise, salad dressings, sauces, ice creams, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

In one embodiment the oil or fat may be an edible oil or fat, aerated and non-aerated whipped products, oil-in-water emulsions, water-in-oil emulsions, margarine, shortening and spreads including low fat and very low fat spreads.

Food Ingredient

The composition of the present invention may be used as a food ingredient.

As used herein the term "food ingredient" includes a formulation which is or can be added to a food or foodstuff. The term food ingredient as used here also refers to formulations which can be used at low levels in a wide variety of products that require emulsifying, gelling, texturising, stabilising, suspending, film-forming and structuring, retention of juiciness and improved mouthfeel.

The food ingredient may be in the form of a liquid or a solid—depending on the use and/or the mode of application and/or the mode of administration.

Enzymes of the Present Invention

The enzyme according to the present invention means an enzyme which is capable of cleaving (or which cleaves) the glycosidic bond of a steryl glycoside and/or an acylated steryl glycoside.

In one embodiment the enzyme may be called a "glycosidase enzyme". The term "glycosidase enzyme" as used herein may mean an enzyme which is capable of cleaving the glycosidic bond of a steryl glycoside and/or an acylated steryl glycoside, preferably under the assay conditions taught below (using steryl glycoside and/or an acylated steryl glycoside substrate).

A glycosidase enzyme would be considered as being an enzyme suitable for use in accordance with the present invention (e.g. a glycosidase enzyme) if under the assay conditions taught below it hydrolyses the steryl glycoside in the steryl glycoside substrate.

Assay to Determine Whether an Enzyme is Capable of Cleaving the Glycosidic Bond of a Steml Glycoside and/or an Acylated Steryl Glycoside in Accordance with the Present Invention:

A steryl glycoside substrate [which may be acylated or unacylated] is prepared using the following steps:

1.0 mg steryl glycoside was scaled in a 7 ml dram glass;
10 µl of 99% ethanol was added;
200 µl of 50mM HEPES buffer pH 7 was added;
300 µl of 10 mM HEPES buffer containing 0.4% Triton X100 was added.

The steryl glycoside is dispersed by agitation for 30 minutes at 40° C. 5×100 µl samples of the steryl glycoside substrate are treated with the enzyme of interest following the protocol below.

TABLE 1

| Sample number | | 1 | 2 |
|---|---|---|---|
| Steryl glycoside substrate | µl | 100 | 100 |
| Water | µl | 10 | |
| Enzyme of interest | µl | | 10 |

100 µl of steryl glycoside substrate is transferred to an Eppendorf tube and placed in a shaking incubator at 40° C. The enzyme or water is added and the reaction mixture is incubated at 40° C. for 16 hours.

The reaction mixture is extracted with 1 ml Chloroform. The chloroform phase was isolated and evaporated to dryness under a steam of Nitrogen.

The sample as redissolved in 200 µl Chloroform:Methanol 2:1 and then analysed by HPTLC (at taught in Example 1). In order to confirm the formation of sterol the samples may also be analysed by GLC (as taught in Example 1) using plant sterol as reference material.

The formation of free sterol from steryl glycoside when it is treated with an enzyme of interest confirms that the enzyme is capable of cleaving the glycosidic bond of a steryl glycoside and/or an acylated steryl glycoside and can be used in accordance with the present invention.

In one embodiment of the present invention, the enzyme may be capable of cleaving (or may cleave) the glucosidic bond of a steryl glucoside and/or an acylated steryl glucoside.

In one embodiment the enzyme may be a "glucosidase enzyme". The term "glucosidase enzyme" as used herein may mean an enzyme which is capable of cleaving the glucosidic bond of a steryl glucoside and/or an acylated steryl glucoside, preferably under the assay conditions taught below.

Assay to Determine Whether an Enzyme is Capable of Cleaving the Glycosidic Bond of Steryl Glucoside and/or Acylated Steryl Glucoside in Accordance with the Present Invention:

A steryl glucoside substrate [which may be acylated or unacylated], e.g. steryl glucoside 98% from Matreya, Pa., is prepared using the following steps:

1.0 mg steryl glucoside was scaled in a 7 ml dram glass;
10 µl of 99% ethanol was added;
200 µl of 50 mM HEPES buffer pH 7 was added;
300 µl of 10 mM HEPES buffer containing 0.4% Triton X100 was added.

The steryl glucoside is dispersed by agitation for 30 minutes at 40° C.

5×100 μl samples of the steryl glucoside substrate are treated with the enzyme of interest following the protocol below.

TABLE 1

| Sample number | | 1 | 2 |
|---|---|---|---|
| Steryl glucoside substrate | μl | 100 | 100 |
| Water | μl | 10 | |
| Enzyme of interest | μl | | 10 |

100 μl of steryl glucoside substrate is transferred to an Eppendorf tube and placed in a shaking incubator at 40° C. The enzyme or water is added and the reaction mixture is incubated at 40° C. for 16 hours.

The reaction mixture is extracted with 1 ml Chloroform. The chloroform phase was isolated and evaporated to dryness under a steam of Nitrogen.

The sample as redissolved in 200 μl Chloroform:Methanol 2:1 and then analysed by HPTLC (at taught in Example 1). In order to confirm the formation of sterol the samples may also be analysed by GLC (as taught in Example 1) using plant sterol as reference material.

The formation of free sterol from steryl glucoside when it is treated with an enzyme of interest confirms that the enzyme is capable of cleaving the glycosidic bond of a steryl glucoside and/or an acylated steryl glucoside and can be used in accordance with the present invention.

In one embodiment the "glycosidase enzyme" as used herein encompasses a "glucosidase enzyme". The term "glucosidase enzyme" as used herein means an enzyme which is capable of carrying out the following the reaction (where the sterol glucoside is in an acylated or unacylated form):

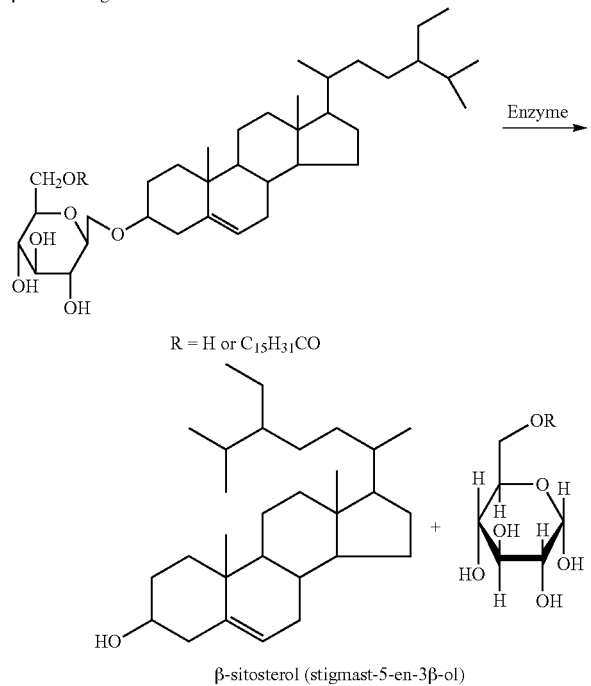

β-sitosterol glucosides

R = H or C$_{15}$H$_{31}$CO

β-sitosterol (stigmast-5-en-3β-ol)

In one embodiment suitably the enzyme may be a glucosidase enzyme.

In one embodiment the enzyme may be a β-glycosidase (e.g. a β-glucosidase) or an amyloglucosidase.

In one embodiment the enzyme for use in the present invention may be a β-glycosidase (e.g. a β-glucosidase).

Suitably, if the enzyme is a β-glycosidase (e.g. a β-glucosidase) the enzyme may be one or more of the following enzymes: a steryl-β-glucosidase (E.C. 3.2.1.104); 1,3-β-glucosidase (E.C. 3.2.1.58) and/or glucan 1,4 β-glucosidase (E.C.3.2.1.74).

In another embodiment the glycosidase enzyme is an amyloglucosidase enzyme (E.C. 3.2.1.3 (in accordance with the Enzyme Nomenclature—Recommendations of the Nomenclature committee of the International Union of Biochemistry and Molecule Biology on the Nomenclature and Classification of Enzyme 1992)). Amyloglucosidase (EC.3.2.1.3) is an important industrial enzyme that is used by the manufacturers of high fructose corn syrup (HFCS). Amyloglucosidase may also be referred to herein as glucan 1,4-α-glucosidase.

The enzyme for use in the present invention may hydrolyse 1,4- and 1,6-alpha linkages in liquefied starch and/or β-linkages. During hydrolysis with amyloglucosidases for example, glucose units are removed in a stepwise manner from the non-reducing end of the substrate molecule. The rate of hydrolysis depends upon the type of linkage as well as the chain length, i.e., 1,4-alpha linkages are hydrolysed more readily than 1,6-alpha linkages, and maltotriose and maltose are broken down at a lesser rate than longer chain oligosaccharides.

The enzyme for use in the present invention may cleave the glycosidic bond of a steryl glycoside as its main activity or as a side activity.

One suitable enzyme for use in the present invention may be a fungal amyloglucosidase, such as an amyloglucosidase obtainable (obtained) from strains of the fungus Aspergillus niger.

Suitable enzymes for use in the present invention may be naturally occurring (and optionally isolated) enzymes or genetically-modified enzymes.

Glycosidase enzymes (or enzymes suitable for use in the present invention) may have a pH optimum of about 3.0 to about 7.0, preferably about 4.0-7.0 and a temperature optimum of about 55 to about 80° C., suitably about 75° C.

In one embodiment a suitable amyloglucosidase enzyme may be AMG 8000™ (obtainable from Danisco A/S—Denmark).

Some enzyme compositions (for example the pectinase composition sold as Grindamyl Ca150™) may have a glycosidase activity (i.e. be capable of cleaving the glycosidic bond of a steryl glycoside). The glycosidase activity of such enzyme compositions may be a side activity, subsidiary to the main (in this case pectinase) activity.

Thus, in one embodiment suitably the enzyme having glycosidase activity (i.e. being capable of cleaving the glycosidic bond of a steryl glycoside) may be a pectinase enzyme composition. In one embodiment the pectinase enzyme having glycosidase activity may be Grindamyl™ Ca 150.

The enzyme for use in the present invention (for instance the glucosidase enzyme) may be used in the present invention at a dosage of about 0.1 mg to about 50 mg enzyme protein per kg oil, preferably about 1 mg to about 10 mg enzyme protein per kg oil.

Degumming

The purpose of edible oil refining is to remove undesirable impurities that affect quality (taste, smell and appearance for example)) and storability.

Due to the wide variety of these impurities-free fatty acids, metal ions, colour compounds, odours, gums etc.—a series of processes of chemical and physical nature are conventionally employed for refining.

Traditionally two processes have been used for degumming of oil which are the physical degumming and the chemical degumming processes.

In the so-called chemical refining, almost all free fatty acid content is removed by initial treatment with a large excess of NaOH. Also the phospholipids content is decreased to a phosphorus level typically below 10 ppm. The oil is subsequently bleached and deodorised.

The so-called physical refining generally consists of a water-degumming step followed by acid degumming, neutralisation, bleaching, steam stripping to remove free fatty acids and deodorisation.

Instead of using acid degumming during physical refinement developments were made to use enzymatic degumming.

The enzymatic degumming process was developed based on the use of pancreatic phospholipase. Because this enzyme was non-kosher the phospholipase was eventually substituted by a microbial phospholipase A1 (Lecitase Ultra™—Novozymes, Denmark) (Oil Mill Gazetteer, Vol 111 July 2005 pp2-4).

The enzymatic process has several advantages over the chemical or the physical degumming processes including cost savings, higher yield and a more environmentally friendly process.

The enzymatic oil degumming process was based on the addition of a phospholipase to an oil which was already water degummed.

In WO2006/008508 lipid acyltransferases were taught for use in enzymatic degumming of edible oils. WO 2006/008508 teaches addition of a lipid acyltransferase to a water-degummed oil or the addition of a lipid acyltransferase to a crude oil without the need for the oil to undergo a water-degumming process.

"Water-degummed oil" may typically be obtained by a conventional "water degumming process" comprising mixing 1-2% w/w of hot soft water with warm (70-90° C.) crude oil (AOCS Introduction to the Processing of Fats and Oils—Table 8—Degumming Processes—http://www.aocs.org/meetings/education/mod3sample.pdf). A rule of thumb is that that amount of water added to crude oil is typically approximately equal to the amount of phospholipids in the crude oil. Usual treatment periods are 30-60 minutes. The water-degumming step removes the phosphatides and mucilaginous gums which become insoluble in the oil when hydrated. The hydrated phosphatides and gums can be separated from the oil by settling, filtration or centrifugation—centrifugation being the more prevalent practice. The essential object in said water-degumming process is to separate the hydrated phosphatides from the oil. The mixing of hot water into the oil, described above, should herein be understood broadly as mixing of an aqueous solution into the oil according to standard water-degumming procedures in the art.

In the conventional water degumming process the main part of the phosphatides are removed in a heavy gum phase. At the end of the water degumming process an oil phase is separated from a gum phase. Although the gum phase can be processed further into commercial products it is essentially viewed as a bi-product of oil refining. It is the oil phase which is commercially important. However, because the phosphatides can be good emulsifiers some oil is inevitably lost in the gum phase during water degumming.

The present invention (e.g. the addition of one or more enzymes to remove steryl glycoside) may be used in combination with degumming (such as chemical degumming, water degumming or enzymatic degumming). The one or more enzymes being added to remove steryl glycoside may be added before, during or after the degumming process.

Combination with other Enzymes

The enzyme, for example the glycosidase enzyme, used in the present invention may suitably be used in combination with a further enzyme.

In one embodiment the enzyme (for example the glycosidase enzyme) used in the present invention may suitably be used in combination with one or more of the following enzymes: an enzyme having lipid acyltransferase activity (E.C. 2.3.1.43); an enzyme having glycolipase activity (E.C. 3.1.1.26), and enzyme having phospholipase A2 activity (E.C. 3.1.1.4), an enzyme having phospholipase A1 activity (E.C. 3.1.1.32). Suitably, enzymes having these activities are well known within the art and include by way of example the following lipases: a phospholipase A1 LECITASE® ULTRA (Novozymes NS, Denmark), phospholipase A2 (e.g. phospholipase A2 from LIPOMOD™ 22L from Biocatalysts, LIPOMAX™ and LysoMax PLA2™ from Genencor), LIPOLASE® (Novozymes NS, Denmark).

In some embodiments it may be beneficial to combine the enzyme for use in the present invention (e.g. the glycosidase enzyme) with a lipid acyltransferase and/or a phospholipase, such as phospholipase A1, phospholipase A2, phospholipase B, Phospholipase C and/or phospholipase D.

Isolated

In one aspect, the enzyme(s) used in the present invention is/are a recovered/isolated enzyme. Thus, the enzyme may be in an isolated form.

The term "isolated" means that the sequence or protein is at least substantially free from at least one other component with which the sequence or protein is naturally associated in nature and as found in nature.

Purified

In one aspect, the enzyme(s) used in the present invention may be in a purified form.

The term "purified" means that the sequence is in a relatively pure state—e.g. at least about 51% pure, or at least about 75%, or at least about 80%, or at least about 90% pure, or at least about 95% pure or at least about 98% pure.

The invention will now be described, by way of example only, with reference to the following Figures and Examples.

Figures

FIG. 1 shows an HPTLC of steryl glycoside (SG) incubated with 1) Water. 2 Grindamyl Ca 150, 3) AMG 8000 (Danisco A/S).

EXAMPLE 1

Removal/Degradation of Steryl Glycoside with enzymes

Materials

Steryl glucoside, 98% from Matreya, Pa..

Enzymes:
  Pectinase, Grindamyl Ca150, item no 1222616
  Amyloglucosidase, AMG 8000, item no 1205013

HPTLC
  Applicator: CAMAG applicator AST4.
  HPTLC plate: 20×10 cm (Merck no. 1.05641)

The plate was activated before use by drying in an oven at 160° C. for 20-30 minutes. Application: 8,0 µl of extracted lipids dissolved in Chloroform:Methanol (2:1) was applied to the HPTLC plate using AST4 applicator. 0.1, 0.3, 0.5, 0.8, 1.5 µl of a standard solution of standard components with known concentration are also applied to the HPTLC plate.

Running-buffer:1: P-ether:MTBE:Acetic acid (50:50:1)
Application/Elution time: 12 minutes.
Running-buffer:4: Chloroform:Methanol:Water. (65:25:4)
Development: 7 cm using Automatic Developing Chamber ADC 2.
Derivatization fluid: 6% Cupriacetate in 16% $H_3PO_4$ After elution the plate was dried in an oven at 160° C. for 10 minutes, cooled and immersed in the developing fluid and then dried additional in 5 minutes at 160° C. The plate was evaluated visually.

GLC Analysis

Perkin Elmer Autosystem 9000 Capillary Gas Chromatograph equipped with WCOT fused silica column 12.5 m×0.25 mm ID×0.1 p film thickness 5% phenyl-methyl-silicone (CP Sil 8 CB from Chrompack).

Carrier gas: Helium.

Injector. PSSI cold split injection (initial temp 50° C. heated to 385° C.), volume 1.0 µl Detector FID: 395° C.

| Oven program (used since 30 Oct. 2003): | 1 | 2 | 3 |
| --- | --- | --- | --- |
| Oven temperature, ° C. | 90 | 280 | 350 |
| Isothermal, time, min. | 1 | 0 | 10 |
| Temperature rate, ° C./min. | | 15 | 4 |

Sample preparation: Extracted samples were dissolved in 0,5 ml Heptane:Pyridin, 2:1 containing internal standard heptadecane, 0.5 mg/ml. 300 µl sample solution is transferred to a crimp vial, 300 µl MSTFA (N-Methyl-N-trimethylsilyl-trifluoraceamid) is added and reacted for 20 minutes at 60° C.

Calculation: Response factors for sterol was determined from pure reference material.

Procedure & Results

The steryl glucoside substrate was prepared using the following steps:

1.0 mg steryl glucoside was scaled in a 7 ml dram glass;
10 µl of 99% ethanol was added;
200 µl of 50mM HEPES buffer pH 7 was added;
300 µl of 10 mM HEPES buffer containing 0.4% Triton X100 was added.

The steryl glucoside was dispersed by agitation for 30 minutes at 40° C.

5×100 µl samples of the steryl glucoside substrate were treated with the various enzymes set out in table 1 following the protocol below.

TABLE 1

| Sample number | | 1 | 2 | 3 |
| --- | --- | --- | --- | --- |
| Steryl glucoside substrate | µl | 100 | 100 | 100 |
| Water | µl | 10 | | |
| Grindamyl Ca 150 | µl | | 10 | |
| AMG 8000, 10% in water | µl | | | 10 |

100 µl of steryl glucoside substrate was transferred to an Eppendorf tube and placed in a shaking incubator at 40° C. The enzyme or water was added and the reaction mixture was incubated at 40° C. for 16 hours.

The reaction mixture was extracted with 1 ml Chloroform. The chloroform phase was isolated and evaporated to dryness under a steam of Nitrogen.

The sample as redissolved in 200 µl Chloroform:Methanol 2:1 and then analysed by HPTLC. A Figure of the TLC plate is shown in FIG. 1.

The TLC chromatogram of FIG. 1 indicates that pectinase (Grindamyl Ca 150) and amyloglucanase (AMG 8000) are able to produce a component with retention time equivalent to sterol, showing that these enzymes degrade steryl glucoside.

in order to confirm the formation of sterol the samples were also analysed by GLC using plant sterol as reference material. The GLC analysis confirmed the formation of free sterol with results shown in table 2

TABLE 2

| GLC analyses of sterol. % based on the amount of steryl glucoside | | |
| --- | --- | --- |
| sample no | Enzyme treatment | Sterol, % |
| 1 | Water | 0.54 |
| 2 | Grindamyl Ca 150 | 15.3 |
| 3 | AMG 8000, 10% in water | 12.8 |

The GLC analysis (table2) confirm the formation of free sterol from steryl glucoside when it is treated with either a Pectinase or Amyloglucosidase.

All publications mentioned in the above specification are herein incorporated by reference. Various modifications and variations of the described methods and system of the present invention will be apparent to those skilled in the art without departing from the scope and spirit of the present invention. Although the present invention has been described in connection with specific preferred embodiments, it should be understood that the invention as claimed should not be unduly limited to such specific embodiments. Indeed, various modifications of the described modes for carrying out the invention which are obvious to those skilled in biochemistry and biotechnology or related fields are intended to be within the scope of the following claims.

The invention claimed is:

1. A method for reducing the amount of steryl glycoside in an oil or fat and/or a biofuel, the method comprising admixing one or more enzymes with an oil or fat comprising steryl glycoside; wherein the one or more enzymes comprises an amyloglucosidase, such that said one or more enzymes degrades the steryl glycoside.

2. The method according to claim 1 wherein the oil is a vegetable oil.

3. The method according to claim 2 wherein the oil is selected from: rapeseed oil, canola oil, soya (soybean) oil, rice bran oil, palm oil, corn oil, cottonseed oil, sunflower oil, safflower oil, nasturtium seed oil, mustard seed oil, olive oil, sesame oil, peanut oil, babassu nut oil, castor oil, palm kernel oil, low erucic acid rapeseed oil, lupin oil, jatropha oil, coconut oil, flaxseed oil, evening primrose oil, jojoba oil, shea nut oil or camelina oil.

4. The method according to claim 1 wherein the biofuel is a biodiesel.

5. The method according to claim 1 wherein the method further comprises a degumming step.

6. The method according to claim 5 wherein the steryl glycoside is degraded before or during the degumming step.

7. The method according to claim 5 wherein the one or more enzymes is admixed with the oil or fat and water during the degumming step.

8. The method according to claim 1 wherein the method further comprises an interesterification step.

9. A method of reducing the amount of steryl glycoside in an oil, fat, and/or biofuel, said method comprising applying one or more enzymes to the oil, fat, and/or biofuel, to degrade the steryl glycoside in the oil, fat, and/or biofuel, wherein the one or more enzymes comprises amyloglucosidase.

10. The method according to claim 9 wherein at least 20% of the steryl glycoside in the oil or fat is removed.

11. The method according to claim 9 wherein the oil is a vegetable oil.

12. The method according to claim 11 wherein the oil is selected from the group consisting of: soya (soybean) oil, rapeseed oil, canola oil, rice bran oil, palm oil, corn oil, cottonseed oil, sunflower oil, safflower oil, nasturtium seed oil, mustard seed oil, olive oil, sesame oil, peanut oil, babassu nut oil, castor oil, palm kernel oil, low erucic acid rapeseed oil, lupin oil, jatropha oil, coconut oil, flaxseed oil, evening primrose oil, jojoba oil, shea nut oil and camelina oil.

13. The method according to claim 9 wherein the biofuel is a biodiesel.

14. An oil or fat or a biofuel obtainable by the method according to claim 1.

15. An oil or fat or a biofuel, which oil or fat and/or biofuel has a reduced amount of steryl glycoside compared with a comparable oil or fat and/or biofuel which has not undergone enzyme treatment in accordance with the method of claim 1.

16. An enzyme composition comprising one or more amyloglucosidase enzymes for use in the production of biofuel.

17. The method according to claim 1 wherein the oil or fat is a biofuel substrate.

18. The method according to claim 1 wherein the method further comprises combining the enzyme with a further enzyme selected from the group consisting of a lipid acyltransferase, a phospholipase, and combinations thereof.

19. The method according to claim 18, wherein the phospholipase is a phospholipase A1, a phospholipase A2, a phospholipase B, a phospholipase C, a phospholipase D or a combination thereof.

20. The method according to claim 9 wherein the oil or fat is a biofuel substrate.

21. The method according to claim 9 wherein the use further comprises combining the enzyme with a further enzyme selected from the group consisting of a lipid acyltransferase, a phospholipase, and combinations thereof.

22. The method according to claim 21, wherein the phospholipase is a phospholipase A1, a phospholipase A2, a phospholipase B, a phospholipase C, a phospholipase D or a combination thereof.

23. The method according to claim 9 wherein the use is in combination with degumming.

24. The method according to claim 9 wherein the steryl glycoside is degraded before or during the degumming step.

25. The method according to claim 5 wherein the degumming step is an enzymatic degumming step.

26. The method according to claim 8 wherein the interesterification step is an enzymatic interesterification step.

27. The method according to claim 9 wherein at least 50% of the steryl glycoside in the oil or fat is removed.

28. The method according to claim 9 wherein at least 80% of the steryl glycoside in the oil or fat is removed.

29. The method according to claim 23 wherein the degumming is enzymatic degumming.

* * * * *